Oct. 5, 1971 S. McGREDY Plant Pat. 3,068
ROSE PLANT
Filed Sept. 9, 1968
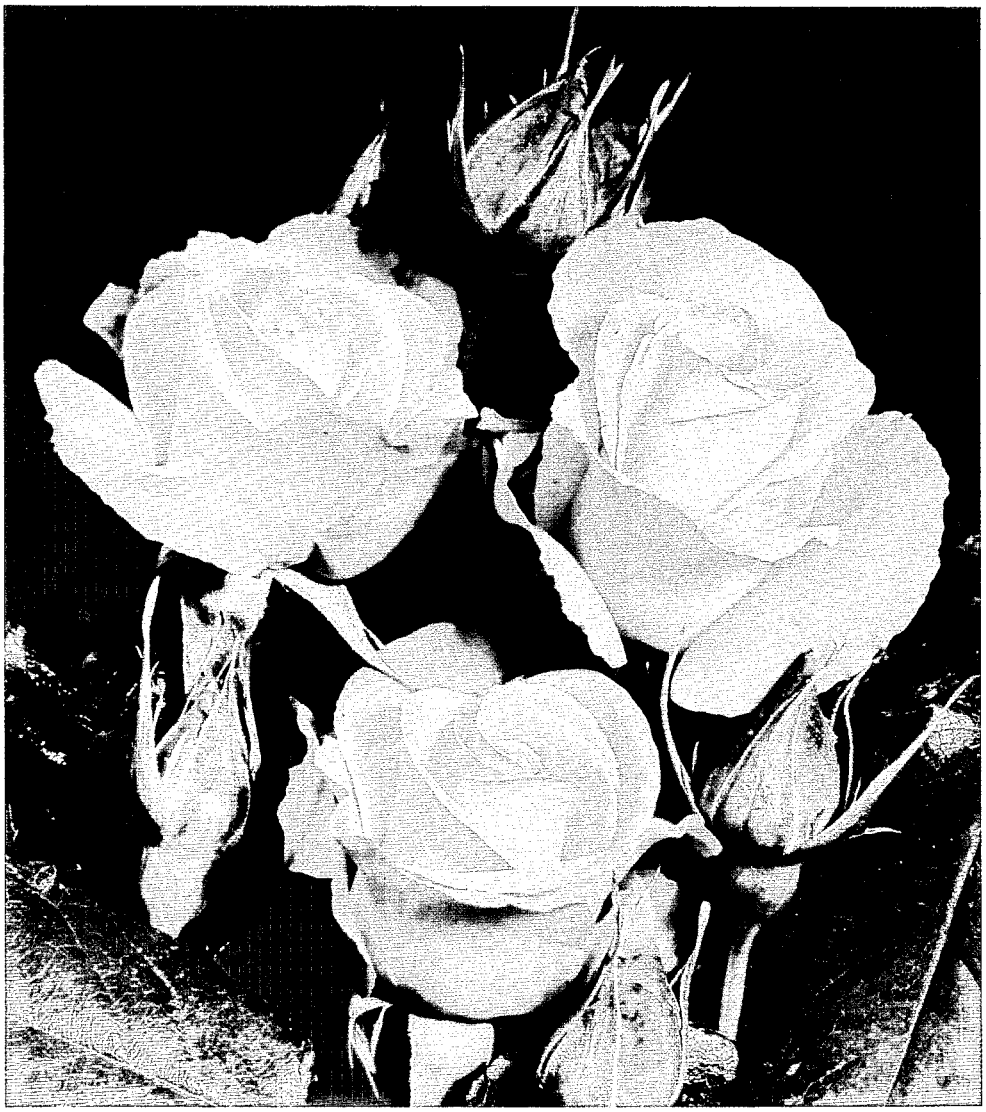

United States Patent Office

Plant Pat. 3,068
Patented Oct. 5, 1971

3,068
ROSE PLANT

Samuel McGredy, % S. McGredy Son, Ltd., Portadown, Northern Ireland

Filed Sept. 9, 1968, Ser. No. 758,634
Int. Cl. A01h *5/00*
U.S. Cl. Plt.—25 1 Claim

The invention relates to a new and distinct variety of rose plant of the floribunda class, originated by me in 1961 as a consequence of a breeding program begun in 1954. The parentage of my new rose plant is as follows: Orangeade × Mischief The object of the cross was to combine the freedom of flowering of Orangeade with the flower size of Mischief.

These objectives were achieved along with other desirable improvements, as evidenced by the following unique combination of characteristics which are outstanding in the new variety and which distinguish it from its parents as well as from all other varieties of which I am aware. My new variety is primarily characterized by: the extremely well formed bright orange small hybrid tea type blooms; the quick repeat flowering habit; the medium size plant of somewhat spreading habit profusely covered in medium green foliage.

Asexual reproduction of my new variety by budding, through a series of annual propagations at Portadown, Northern Ireland, shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container grown budded plants under greenhouse and field conditions at Santa Rosa, Calif.

Strong, sturdy, vigorous plant, somewhat spreading habit, of medium height, 20–30" with moderate to abundant branching. The plant has thorns and a few prickles. The bases of the thorns variable about 3/16–6/16" tall x 1/16"–3/16" wide x 3/16"–3/8" long. They occur plus or minus 12 per 3" of stem at 3rd node below flower.

Abundant foliage, smooth, leathery and semi-glossy; Spinach Green (HCC 0960) heavily overlain with Beetroot purple (HCC 830) when young; duller than above Spinach Green (HCC 0560) heavily overlain with Garnet Lake (HCC 828/2) on lower side when mature upper side Ivy Green (HCC 0001060/2), Sage Green (HCC 000861/1) lower side. Leaflets 3–7, average 5, about 1–1 9/16" wide x 1 3/8"–2 3/8" long. The shape of the leaf is odd-pinnate, the leaflets being generally ovate, accuminate and with serrated margins. The rachis of the leaf is about 1 3/8"–2 5/16", petiole about 1"–1 1/2" with ribs and veins conspicuous.

The flower bud is small to medium 1–1 1/2" long and 5/8"–1 1/16" wide, long and pointed becoming urceolate. When sepals first begin to divide the bud is Rose Opal (HCC 022), when sepals begin to unfurl the bud is Rose Opal (HCC 022), opens slowly. The hypanthium is funnel form, of medium size, 3/8" wide x 3/8" long, smooth outside, hairy inside. The peduncle is erect with some small prickles; 2–2 3/4" long, Lettuce Green (HCC 861).

The flower is medium about 3–3 7/8" in diameter and about 1 3/4–2 1/2" in depth, fragrant, of classical hybrid tea bloom, high centered which flattens as bloom matures. The sepals are not ornate, not hooded over bud: slightly branched (i.e. 2 branches on every other sepal, curl back as they unfurl). Spinach Green (HCC 0960/3) inside and Spinach Green (HCC 0960/1) outside. The petals are obovate, leathery to velvety giving a velvety appearance. There are 20–30 petals, imbricated, about 1–2 1/8" wide x 1 1/8"–2" long (inner petal smaller and crinkled). The outer petal light Delft Rose (HCC 020/1) becoming deeper Delft Rose (HCC 020/2) at base with a 1/4" quadrant of Uranium Green (HCC 63/3) at base; the inside petal is the same as outside only streaked with Uranium Green (HCC 63/3) and Delft Rose (HCC 020). Reverse same as above, Mature bloom fades slightly. Blooms borne 1–5 on strong canes, persist 5–10 days on stems. Petaloides are 25–30, 3/16"–1 1/16" wide by 1/2"–1 1/4" long the color same as petals, streaked with Uranium Green (HCC 63/3) and Delft Rose (HCC 020). Flower resistant to mildew, rust and blackspot as observed in Santa Rosa, Calif. The pistils plus or minus 110 in number, plus or minus 1/4" long, same coloring as petals only a little darker Delft Rose (HCC 020). The Stamens, anthers plus or minus 150 in number, 1/2" long, whorled arrangement. The filaments 7/16" long, same coloring as petals only with a yellow tint. The stigmas are creamy white in color. The ovaries are ordinary. The variety is highly fertile, the fruit round and orange.

Having thus disclosed my invention, I claim:

1. A new and distinct variety of rose plant of the floribunda class substantially as herein shown and described primarily characterized by: the extremely well formed, bright orange, small hybrid tea type blooms; the quick repeat-flowering habit; the medium size plant of somewhat spreading habit, profusely covered in medium green foliage.

No references cited.

ROBERT E. BAGWILL, Primary Examiner